United States Patent [19]

Guardino et al.

[11] Patent Number: 4,610,961
[45] Date of Patent: Sep. 9, 1986

[54] INHIBITION OF REDUCTION ACTIVITIES OF LEUKOCYTES

[75] Inventors: Robert F. Guardino, Rochester; Robert T. Belly, Webster, both of N.Y.

[73] Assignee: Eastman Kodak Company, Rochester, N.Y.

[21] Appl. No.: 453,033

[22] Filed: Dec. 27, 1982

[51] Int. Cl.[4] .................. C12Q 1/04; C12Q 1/06; A61K 47/00; G01N 31/00
[52] U.S. Cl. ........................... 435/34; 435/39; 435/805; 436/17; 424/7.1
[58] Field of Search ............ 435/4, 29, 34, 805, 435/39; 424/7.1; 436/17

[56] References Cited

U.S. PATENT DOCUMENTS

| | | | |
|---|---|---|---|
| 3,415,718 | 12/1968 | Forkman et al. | |
| 3,928,139 | 12/1975 | Dorn | 435/34 |
| 3,971,703 | 7/1976 | Picciolo et al. | 435/8 |
| 3,992,158 | 11/1976 | Przybylowicz | 422/57 |
| 4,026,767 | 5/1977 | Shih et al. | 435/34 X |
| 4,212,948 | 7/1980 | Dorn | 435/296 |
| 4,258,001 | 3/1981 | Pierce et al. | 422/56 |
| 4,296,202 | 10/1981 | Berger et al. | 435/29 |
| 4,297,238 | 10/1981 | Vormbeck et al. | 252/408 |
| 4,331,760 | 5/1982 | Berger et al. | 435/19 |
| 4,525,453 | 6/1985 | Guardino et al. | 435/34 |

FOREIGN PATENT DOCUMENTS 2059990 4/1981 United Kingdom.

OTHER PUBLICATIONS

Chem. Abstr. 74 No. 15, paragraph 75277g 1971.
Chem. Abstr. 36 No. 3 col. 1059/9–1060/1 1941.
Thore et al., "Detection of Bacteriuria by Luciferase Assay of Adenosine Triphosphate," J. Clin. Microbiology, 1:1–8, 1975.
Uroscreen (Triphenyltetrazolium Chloride), "A Simple Semiquantitative Diagnostic Screening Method for Presumptive Bacteriuria," Pfizer, Diagnostics Div., N.Y. (Brochure), 1974.
K. Kakinuma et al., "Effect of Ionic Sites of Surfactants on Leukocyte Metabolism," J. Biochem., 79:795–802, 1976.
Graham et al., "Metabolic and Morphological Observations on the Effect of Surface-Active Agents on Leukocytes," J. Cell Biol. 32:629–642, 1967.
Berger et al., "Azo Dye Esters and Their Use in Diagnostic Agents for Detection of Leukocytes in Body Fluids" Chem. Abst. vol. 93 65418g 1980.
Kolehmainen et al., "Selective Determination of Metabolites in Soma or Microbial Cells" Chem. Abst. vol. 90, 83317r 1979.
Berger et al., "Diagnostic Agent for Detecting Leukocytes in Body Fluids and Suitable Chromogens" Chem. Abstr. vol. 93, 22139z, 1980.

Primary Examiner—Thomas G. Wiseman
Assistant Examiner—Elizabeth C. Weimar
Attorney, Agent, or Firm—Arthur H. Rosenstein

[57] ABSTRACT

A means of selectively lysing leukocytes but not bacteria is described. This technique is useful in conjunction with a reduction analysis to provide a rapid interference-free determination of either leukocytes or bacteria in clinical samples. The method is adaptable to a solution or dry element mode.

24 Claims, No Drawings

INHIBITION OF REDUCTION ACTIVITIES OF LEUKOCYTES

BACKGROUND OF THE INVENTION

1. Field of the Invention

The present invention relates to clinical analyses of aqueous samples in which a reducible substrate is used as an indicator to detect the presence of bacteria or leukocytes. In particular, it relates to a method of improving the specificity of reduction assays by removing the leukocyte response through selective lysis of leukocyte cells.

2. General History

The increased availability of specific and effective antibiotics has produced a commensurate need for more rapid methods of clinical diagnosis of infection. The standard technique of diagnosing infection was to culture a sample suspected of containing the infecting bacteria, but this is a time-consuming process requiring skilled personnel. This has lead to a search for chemical methods of detecting and quantifying bacteria in body fluids.

One known method involves the use of a reducible chromogen as an indicator. This method known as Uroscreen, uses a reagent, triphenyltetrazolium cloride, and is described in "A Simple Semiquantitative Diagnostic Screening Method for Presumptive Bacteriuria," Pfizer, Diagnostics Division, New York (Brochure), 1974. Uroscreen TM is a dry, buffered reagent which is reduced in the presence of large numbers of bacteria to a pink-red insoluble precipitate after four hours of incubation. The manufacturer notes that highly colored or bloody urine may obscure the results.

There is a serious problem with this type of procedure. Clinical infections are often accompanied by a significant number of leukocytes which would additionally be present in samples for analysis. Furthermore, a significant number of leukocytes may be present in samples such as urine even in the absence of infection. Unfortunately, leukocytes, are also capable of reducing known chromogens such as those found in the Uroscreen TM method and thus, leukocyte reduction of the chromogen produces false positive results. This renders the known bacterial assays unreliable and makes quantification impossible.

Thus, the problem is to provide a fast and leukocyte interference-free assay of bacteria.

SUMMARY OF THE INVENTION

In the present invention, leukocyte interference in a reduction-type bacterial assay is eliminated through inhibition of leukocyte reducing ability by lysing the leukocyte. It has been discovered that, upon lysis, leukocyte reducing activity is substantially inhibited. When selective means which lyse leukocytes but leave bacterial cells intact are used, an assay for bacteria shows only bacterial reduction activity. Thus, the interference problem has been solved and a fast and leukocyte interference-free assay of bacteria has been found. This assay is made possible by the use of a selective leukocyte lysing agent and a reducible substrate indicator. The elimination of the false positive factor allows quantification of the results. The added specificity gives the basic bacterial assay procedure of the known chromogenic methods a more general utility, making it adaptable to determinations of the gram-type of bacteria present and as a general means for eliminating the need for growth in microbial assays. This procedure also allows a good assay for leukocytes.

One embodiment of this invention is a method for the detection of bacteria in an aqueous sample. The method comprises selectively lysing the leukocytes through means such as sonication or contact with a surfactant and adding a reducible substrate such as a chromogen as an indicator. After incubation, the amount of reduction indicated is a measure of bacterial presence.

Another embodiment of this invention is a method for the detection of leukocytes in an aqueous sample. This requires two separate analyses using a reducible substrate as an indicator. In one, the leukocytes are inhibited through selective lysis and in the other, the leukocytes remain intact. The difference in results between the two analyses represents a measure of leukocytes present.

Still another embodiment of this invention is a more specific method of assaying bacteria which allows determination of gram-positive or gram-negative types of bacteria. This method comprises the use of two surfactants in combination, one which causes selective leukocyte cells lysis and an inhibitor of the reducing ability of either gram-positive bacteria or gram-negative bacteria A reducible substrate is added as an indicator. The amount of reduction indicated is a measure of the type of bacteria not affected by the surfactant.

All of the above-described embodiments are performed either in solution or on a dry test element. The dry test element of this invention comprises a support layer and a reagent layer A specific element for the detection of bacteria comprises a reagent layer which incorporates a reducible chromogen and a sufficient amount of surfactant to selectively lyse leukocytes but not bacteria. The method for the detection of leukocytes using a dry element requires two different test elements, one in which the reagent layer incorporates a reducible chromogen but no surfactant which selectively lyses leukocytes and one in which the reagent layer incorporates both a reducible chromogen and a surfactant that lyses leukocytes. For the determination of gram-negative bacteria, the element includes a reducible chromogen plus two surfactants, one which selectively lyses leukocytes and the other which selectively inhibits the reducing ability of gram-positive bacteria. For the determination of gram-positive bacteria, the element incudes a reducible chromogen plus a surfactant that selectively lyses leukocytes and a salt that selectively inhibits the reducing ability of gram-negtive bacteria. The method required for all of these assays is to spot the element with sample fluid and, after incubation, to detect the amount of color produced.

DESCRIPTION OF THE PREFERRED EMBODIMENTS

This invention represents a procedure for analyzing aqueous samples which may contain bacteria or leukocytes or both. Such samples generally comprise body fluids such as urine, blood, and cerebrospinal fluid. The analysis is performed in order to assay the cellular constituents of the sample as a tool in the diagnosis of disease and infection. This invention allows differentiation of various cellular constituents in an aqueous clinical specimen.

It has been found that lysis of leukocytes by any means inhibits the reducing activity of the cells. By "cell lysis" is meant the destruction or disintegration of the cell unit. The reduction inhibition occurs with complete or incomplete lysing of the cell membranes.

This invention employs methods of selective lysis, that is, lysis of leukocytes but not bacteria. Selective lysis is possible because of structural differences between the two types of cells. Bacteria are surrounded by a rigid cell wall while leukocytes lack this rigid structure. Some chemical and mechanical manipulations which disrupt the rigid structure of leukocytes do not affect the integrity of the cell wall.

Examples of means of selectively lysing leukocytes include treatment of the sample with ultrasound vibrations, a technique called sonication. This treatment for selective lysis is well known in the art. Leukocytes may be selectively lysed by sonication using controlled conditions of power output and duration of exposure. Appropriate equipment for sonication includes an ultrasonic power supply (e.g. Branson model J-17A, Branson Ionic Power Co., Danbury, CT) equipped with a sonic converter and horn assembly, and a microtip (available from Heat Systems - Ultrasonics, Inc., Plainview, N.Y.). The procedure for sonicating to achieve selective lysis of leukocytes comprises: exposing samples to two 20-second periods of sonication using a 100-watt output while the sample is held in an ice bath.

The preferred method of selective leukocyte lysis is through contact of the cells with surfactants. These surfactants are used in concentrations and quantities sufficient to cause leukocyte cell lysis, but not bacterial cell lysis. Preferred concentrations are approximately between 0.01% and 1.0% of the surfactant solution.

The most preferred selective leukocyte lysing surfactants are neutral or nonionic surfactants. Some examples of these are: octylphenoxy polyethoxyethanol (Triton X-100), n-nonyl phenoxy polyglycerol (Olin 10G), polyethylene glycol ether of a secondary alcohol (Tergitol 15-S-12), polyoxyethylene (23) lauryl ether (Brij 35), and polyoxyethylene (8) stearate (Myrj 45).

Certain anionic surfactants are useful as selective leukocyte lysing agents. Examples of these are saponin and digitonin.

The means for selectively lysing leukocytes and determining sufficient concentrations of surfactants to selectively lyse leukocytes must conform to the following test. The means for lysing is tested by comparing the effect of that means on the reducing activity of leukocytes to its effect on the reducing activity of bacteria. This procedure for evaluating the selectivity of potential leukocyte reduction inhibitors follows.

To determine if a treatment is useful for lysing leukocyte cells, 1 mL of leukocyte suspension (containing approximately $0.5 \times 10^6$ cells/mL) in phosphate buffered saline (PBS) (0.05 M potassium phosphate buffer in 0.85% sodium chloride) is pipetted into each of two assay tubes. If a particular sonication technique is being tested, one of the tubes is treated with ultrasound while the other remains untreated as a control. One mL PBS, pH 7.0, is added to each tube. For testing the lysing effect of a particular surfactant, 1 mL of leukocyte suspension is pipetted into each of two assay tubes. One tube receives 1 mL PBS containing the surfactant at the concentration being tested (such as between 0.01 gram percent and 1.0 percent) while the other tube, the control, receives 1 mL PBS. To all tubes are added 50 microliters 10% glucose and 50 microliters PMS (phenazinemethosulfate) (1 mg/mL methanol). The tubes are agitated on a mixer such as a Vortex (VWR, Rochester, N.Y.). Fifty microliters of MTT (3-(4,5-dimethyl-2-thiazolyl)-2,5-diphenyl-2H-tetrazolium bromide) (10 mg/mL methanol) are added to each tube, and the solutions are mixed, then incubated at 37° C. for 30 minutes. Following incubation, the tubes are examined for MTT reduction, which is indicated by the presence of a purple color. If the suspension which was treated by sonication or with surfactant shows little or no reduction while the control shows considerable reduction, then the means for lysis meets the first part of this test. To determine whether an inhibitor is selective or whether it affects bacteria as well as leukocytes, 2.5 mL of bacterial cell suspension in PBS (approximately $10^9$ cells/mL) is pipetted into each of two assay tubes. Appropriate organisms in the suspension may include: *Escherichia coli, Proteus vulgaris, Pseudomonas aeruginosa, Staphylococcus aureus,* and *Streptococcus faecalis.* One tube receives the same test treatment as the leukocyte suspension above, that is, either sonication or a surfactant in 2.5 mL PBS, while the other remains untreated as a control, receiving only 2.5 mL PBS. To each tube is added 100 microliters each of 10% glucose, PMS (1 mg/mL methanol) and MTT (10 mg/mL methanol). The solutions are mixed and visually examined for MTT reduction after incubation at 37° C. for 15 minutes. As above, reduction activity is evidenced by formation of a purple color. Sonication techniques and surfactants which are means for selective leukocyte lysis and included in this invention are those which, according to the above-described test, inhibit leukocyte reduction (i.e. little or no color formation in test suspension, color formation in control) but do not inhibit bacterial reduction activity (color formation in both test and control suspensions).

The lysing techniques described above are used in conjunction with assays which are based on the reducing properties of cells. Actively metabolizing cells are engaged in a complex series of oxidation-reduction reactions. Chemicals added to a cell-containing medium may be acted upon by the cells in the course of their metabolic processes. A reduction analysis or reduction-type assay is a test which comprises adding to a sample a reducible indicator which is chemically reduced by the cells being tested, to yield a detectable end product. An example of this type of test is described in U.S. Pat. No. 3,415,718 of Forkman and Dahlquist.

Any compound which is reduced by cells to yield an end product detectable by any means such as colorimetry, potentiometry, or fluorescence is useful in a reduction analysis and is referred to herein as a "reducible indicator". Chromogens are preferred reducible indicators. The term "chromogen" as used herein denotes a reducible indicator that produces a colored end product upon reduction. This invention is not limited to the indicator used in the methods described herein. An appropriate indicator for the reduction analysis of this invention is any compound which is reducible by bacteria and leukocytes and which yields a detectable end product.

The compound capable of being reduced to a detectable species, employed in the practice of this invention, can be any material that, in its oxidized form, is capable of being reduced by microorganisms, in the absence of any reduction-inhibiting materials, to produce a detectable product. Such detection may, for example, be achieved by potentiometric means. Preferably, the detectable species will represent a material that is directly detectable by radiometric means. As used herein, the term "radiometric means" is defined to include any one of various analytical sensing means that employs radiation to provide an analytical result.

A partial listing of various detectable species that are directly detectable by radiometric means includes (a) colorimetrically detectable materials, such as colorants (i.e. dyes or pigments) that have extinction coefficients or absorption spectra that can be used to determine their presence or concentration using conventional colorimetric detection devices; and (b) radiation emissive materials, such as fluorescent materials, e.g. a fluorescent probe, that can be detected by a device capable of sensing radiation emitted from such materials.

The use of dyes or, preferably, dye precursors, as the detectable species is preferred. The use of a dye presents several possibilities: (1) the redox reaction may cause it to change from one color to another, (2) a colored dye may become colorless, or (3) a colorless material, i.e. a dye precursor, may become a colored dye. Alternative (3) is the one most preferred in the practice of this invention because the generation of color is generally more easily detectable than its disappearance.

Examples of dyes that can be used in the practice of this invention are methylene blue, dichloroindophenol, resazurin, and various tetrazolium compounds that, upon reduction, become colored formazan dyes, such as 3-(4,5-dimethyl-2-thiazolyl)-2,5-diphenyl-2H-tetrazolium bromide, 2,3,5-triphenyl-2H-tetrazolium chloride, tetranitro blue, tetrazolium chloride, and nitrotetrazolium violet. Tetrazolium salts are the preferred dye precursors for use in the present invention.

Tetrazolium salts useful in the present invention are those having general Formula I and that can be reduced to formazan dyes of general Formula II as follows:

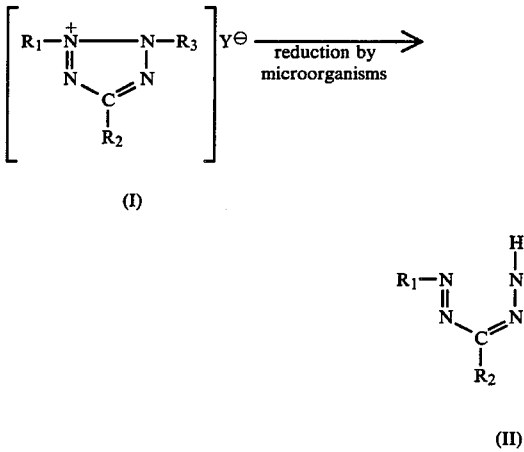

(I)

(II)

In the above Formulas I and II, $Y^{\ominus}$ *represents an anion*; $R_1$, $R_2$, and $R_3$ each represent an aryl or a heterocyclic substituent (preferably containing from 5 to 6 atoms, preferred hetero atoms being N, S, O, and Se), such as phenyl, substituted phenyl, naphthyl, substituted naphthyl, a substituted or unsubstituted thiazolyl, benzothiazolyl, oxazole, benzoxazole, selenazole, or benzoselenazole radical; $R_2$, in addition, can represent an alkyl group (e.g. methyl, butyl, hexyl, dodecyl, etc.) or a substituent (including acidic substituents) such as, for example, —H, —OH, —COOH, —SO$_3$H, —SH, —NO$_2$, etc., or any other substituent cited as being present in this position of the formazan or the tetrazolium salt in Chem. Rev., 55, 355–483 (1955); and the substituents $R_1$ and $R_3$ may contain an electron-sharing group capable of forming metal chelates or complexes.

Examples of such chelating groups or complexes are primary, secondary, and tertiary amino, imino, substituted imino, oxime, thioether, keto, thioketo, hydroxyl, mercapto, carboxyl, sulfo, and phospho, alkoxy groups or complexes.

The tetrazolium salts useful in this invention also include bis-compounds of the general Formula III that can be reduced by microorganisms to produce formazan of Formula IV:

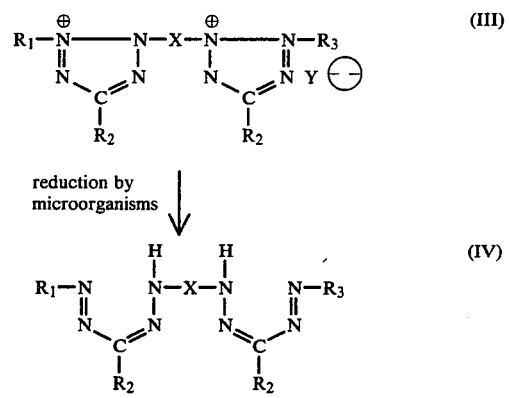

wherein $Y^{\ominus}$ represents an anion and X an alkylene or arylene group; and $R_1$, $R_2$, $R_3$, each represents a substituent as described above in connection with Formulae I and II.

Specific examples of tetrazolium salts that are useful in carrying out this invention are:

(a) triphenyl tetrazolium chloride (TTC);

(b) 2,2'-(p-diphenylene)-bis(3,5-diphenyl)tetrazolium chloride (also known as neotetrazolium chloride or NT);

(c) the methoxy derivative of NT (also known as BT blue tetrazolium);

(d) 2-p-iodophenyl)-3-(p-nitrophenyl)-5-phenyl tetrazolium chloride (INT);

(e) 2,2'-di-p-nitrophenyl-5,5'-diphenyl-3,3'-(3,3'-dimethoxy-4,4'-biphenylene)ditetrazolium chloride (also known as nitro-BT);

(f) 2,2',5,5'-tetra-p-nitrophenyl-3,3'-(3,3'-dimethoxy-4,4'-biphenylene)-ditetrazolium chloride (also known as tetra-nitro BT or TNBT);

(g) 3-(4,5-dimethyl-thiazolyl-2)-2,5-diphenyl tetrazolium bromide (MTT);

(h) 2,2'-di-(3-nitrophenyl)-5,5'-dimethyl-3,3'-(4,4'-biphenylene) ditetrazolium chloride (also known as yellow tetrazolium or YT);

(i) 2,3,5-tri(p-nitrophenyl)-tetrazolium bromide (TNTTC);

(j) 2-phenyl-3-(3-methoxy-4-phenyl)-5-(p-nitrophenyl)-tetrazolium chloride (also known as half nitro BT); and (k) 2,5-di(p-nitrophenyl)-3-(3-methoxy-4-phenyl)tetrazolium chloride (also known as half TNBT).

More detailed information about these compounds can be found in *Histochemistry, Theoretical and Applied*, by A. G. E. Pearse, Volume 2, Third Edition, pp. 880–883, Churchill Livingstone, Edinburgh and London, 1972.

A solution-mode assay for bacteria in an aqueous sample according to this invention employs the above-described techniques of leukocyte inhibition through selective lysis and a subsequent reduction analysis. A sample of a body fluid such as urine is obtained for testing. Preferably, it is fresh and homogeneous. A preferred means for inhibiting leukocytes is to use one of the above-mentioned neutral or anionic surfactants, added at a concentration effective to cause selective lysis of leukocytes but not bacteria. A reducible substrate which yields a detectable end product, preferably a chromogen, is added as an indicator. The presently preferred chromogen indicator is MTT, used at a preferred concentration of $5 \times 10^{-5}$ M to $5 \times 10^{-4}$ M. It is preferable to add an electron transfer agent which is capable of transferring electrons from the cells to the substrate, thus speeding the reduction reaction. Appropriately substituted phenazines, benzoquinones and naphthoquinones having a reduction potential between that of the dye and that of the cell are useful. An example of a useful electron transfer agent is phenazinemethosulfate (PMS), used in the preferred range of $7 \times 10^{-5}$ to $4 \times 10^{-4}$. Other useful electron transfer agents include phenazineethylsulfate, meldola blue, menadione, trimethylbenzoquinone and the like.

Other useful addenda for the assay include glucose or other metabolizable compounds to provide an energy source for cellular reactions.

The amount of chromogen reduction can be detected in several ways, depending on the need for precision. If a visual examination of color formation will provide sufficient information, the sample tube is mixed, then incubated, preferably for 30 minutes or less at 20° C. to 45° C. and then visually examined. A more precise and quantitative reading of the results can be obtained by measuring absorbance with a spectrophotometer such as the Perkin-Elmer 572. The amount of chromogen reduction is defined as the change in absorbance at 540 nm over 10 minutes at 37° C. A standard curve is useful with the absorbance method. Such a curve is constructed by plotting absorbance values obtained by subjecting suspensions containing known quantities of bacteria to the above-described reduction assay procedure. Absorbance values from clinical samples are then compared with the standard curve to give a reading of the number of bacteria present.

A solution assay for leukocytes in an aqueous sample employs the same techniques and preferred addenda as the bacterial assay but requires two steps. One portion of the sample is tested with the indicator without lysing. The amount of reduction detected by either visual examination or absorbance represents total cellular activity in the sample including both bacteria and leukocytes. A second portion of the sample is analyzed according to the procedure used in the bacterial assay above, yielding a result which represents bacterial reduction alone, leukocyte reduction having been inhibited by lysis. The difference in chromogen reduction between the two samples represents leukocyte activity.

Although detection of bacterial presence is a valuable tool in clinical diagnosis, identification of the microorganisms involved may also be necessary. One of the primary characteristics of a microorganism is its reaction to the well-known Gram's stain technique. Accordingly, bacteria fall into two groups, known as gram-positive and gram-negative. The ability to distinguish between these two types is a useful determination which bears upon the choice of antimicrobial therapy and techniques for further identification of the bacteria.

A preferred embodiment of the present invention is a bacterial assay which includes gram-differentiation by combining the above-described leukocyte reduction inhibition technique with selective inhibition of gram-positive bacteria as described in U.S. application Ser. No. 436,877 filed Oct. 26, 1982 and entitled "The Use of Anionic Surfactants to Prevent the Reduction of Compounds By Gram-Positive Microorganisms" by Guardino and Belly, now U.S. Pat. No. 4,525,453. The analysis as performed in solution employs the methods already described with the addition of a second surfactant such as sodium 3,9-diethyl tridecanol sulfate (Tergitol 7). Tergitol 7 is an inhibitor of reduction activity in gram-positive organisms when used in a concentration range of approximately 0.1% to 10% (v/v). It is best used in a pH range of 7 to 8.5. A reducible substrate, preferably a chromogen, is added as described above. Preferred addenda include an electron transfer agent, phenazine metosulfate glucose, Triton X-100 and Tergitol 7. Chromogen reduction indicates the presence of gram-negative bacteria in the sample. This procedure is also useful in conjunction with inhibitors of gram-negative organisms, such as high salt concentration, for the detection of gram-positive bacteria.

The assay composition comprises a reducible indicator, preferably a chromogen, present in the range of $10^{-4}$ to $10^{-6}$ M, a surfactant which selectively lyses leukocytes but not bacteria present in the appropriate amount to cause selective lysis, plus an aqueous sample suspected of containing leukocytes and/or bacteria. The preferred pH range of such a composition is 7.5 to 8.2, maintained by buffers such as inorganic phosphate. It is preferable also to include other addenda described as useful above, e.g. electron transfer agent ($10^{-4}$ M to $10^{-6}$ M) and glucose (0.1 to 1.0 g %).

The aforementioned assays are preferably performed in a dry mode with the use of a test element such as described in U.S. Pat. No. 3,992,158 of Przybylowicz and Millikan or U.S. Pat. No. 4,258,001 of Pierce and Frank. Such an element comprises a support, preferably a spreading layer, and a reagent layer. The reagent layer can either be a combination reagent/spreading layer or a separate spreading layer can overlay the reagent layer. The support comprises any suitable material described in the aforementioned patents, such as poly(ethylene terephthalate).

A subbing layer is preferably included between the support and reagent layers. Examples of materials useful as a subbing layer are a polymer such as poly(acrylamide-co-N-vinyl-2-pyrrolidone) or poly(acrylamide) and a surfactant such as Zonyl FSN.

The reagent layer incorporates a reducible chromogen such as MTT (approximately 0.1 g/m$^2$ to 0.2 g/m$^2$) and an electron transfer agent such as PMS (approximately 0.01 to 0.1 g/m$^2$). The elements used for particular assays may require the incorporation of different surfactants as inhibitors in the reagent layer. An element designed to assay all bacteria contains an anionic or neutral surfactant as a selective inhibitor of leukocyte reduction activity (approximately 1 g/m$^2$ to 10 g/m$^2$). A leukocyte assay requires two different test elements, one containing no inhibitory surfactant and one identical to the bacterial assay element above containing a leukocyte-inhibiting surfactant. The element used in a gram-differentiation assay incorporates two surfactants, one which selectively inhibits leukocytes (approximately 1 g/m$^2$ to 10 g/m$^2$) and one which selectively inhibits one of the gram-types of bacteria (approximately 1 g/m$^2$ to 10 g/m$^2$). A preferred spreading/reagent layer comprises the polymeric structure described in U.S. Pat. No. 4,258,001 of Pierce and Frank, preferably poly(vinyltoluene-co-p-t-butylstyrene-co-methacrylic acid). The reagent layer can be located anywhere within the element, and in a preferred embodiment, the reagents are incorporated in the spreading layer.

A procedure for using these dry test elements comprises spotting the reagent layer surface with sample, preferably about 10 microliters. Just before spotting, it is preferable to add 0.2 g % of glucose to the sample. Detection of chromogen reduction is achieved by measuring the reflectance density ($D_R$) at approximately 540 nm on a reflectance densitometer. Blank control elements are then spotted with fluid comprising PBS and glucose but no cells. There are at least two alternative methods of incubation and detection. In one, the $D_R$ at 550 nm is measured for 10 minutes at 37° C. The change in reflectance density over a 10-minute period ($\Delta D_R$ 10 minutes) is calculated by subtracting the $D_R$ at 0 minutes from the $D_R$ at 10 minutes and then subtracting the $\Delta D_R$ 10 minutes of the control. In another method, after spotting the dry element, the element is incubated in a equilibrated moist chamber at 20° C. to 45° C. for a suitable time period. After incubation, the $D_R$ is measured. The $\Delta D_R$ at 15 minutes is calculated by subtracting the $D_R$ at 15 minutes of a control lacking cells from the $D_R$ at 15 minutes of the test sample. In either case, the leukocyte assay is performed by subtracting the result of the element containing the leukocyte inhibitor from the result of the element containing no inhibitor.

A standard curve correlating reflectance density with quantity of cells present can be constructed. Suspensions are prepared with known quantities of leukocytes and bacteria and measured according to the procedure described. Thus, the assay in dry mode is fast and quantitative.

The following examples further illustrate the invention.

EXAMPLES

The following materials were used in the examples:

Leukocyte suspensions were prepared from human blood.

Bacterial suspensions were prepared from organisms obtained from the American Type Culture Collection in Rockville, Md.

Phenazinemethosulfate (PMS), saponin, digitonin, polyoxyethylene (20) sorbitan monooleate (Tween 80), sodium 3.9 diethyl tridecanol sulfate (Tergitol 7), polyethylene glycol ether of a secondary alcohol (Tergitol 15-S-12), and octylphenoxy polyethoxy ethanol (Triton X-100) were purchased from Sigma Chemical Co., St. Louis, Mo.

Polyoxyethylene (23) lauryl ether (Brij 35) and polyoxyethylene (8) stearate (Myrj 45) were obtained from ICI Americas, Inc., Wilmington, Del.

The fluorochemical surfactant Zonyl FSN was acquired from E. I. DuPont de Nemours and Co., Wilmington, Del.

N-nonyl phenoxy polyglycerol (Olin 10G) was purchased from Olin Corp., Stamford, Conn.

All other chemicals were reagent grade and were obtained from Eastman Kodak Company, Rochester, N.Y.

Solution-mode assays were performed with use of a Perkin-Elmer 572 spectrophotometer equipped with 5-cell programmer and temperature control.

A modified conventional reflectance densitometer was used in the dry element assays.

Multilayer dry test elements were prepared according to the following format:
 I. Spreading/Reagent Layer
  polymeric bead and binder,
  surfactant,
  3-(4,5-dimethyl-2-thiazolyl)-2,5-diphenyl-2H-tetrazolium bromide (MTT) (0.11 g/m$^2$) and an electron transfer agent.
 II. Subbing Layer
 III. Support Layer
  poly(ethylene terephthalate)

EXAMPLES 1-7

Selective Inhibition of Leukocyte Reduction Activity Through Cell Lysis

Solutions comprising leukocytes in PBS, pH 7.0, prepared from human blood, were treated with anionic or neutral surfactants, or sonication. Microscopic examination indicated complete lysis of the cells. The solutions were then assayed for reduction activity.

One mL of leukocyte suspension was pipetted into assay tubes. One mL PBS, pH 7.0, or 1 mL PBS containing a surfactant was added to the assay tubes. To all tubes were added 50 μL 10 g % glucose and 50 μL PMS (1 mg/mL methanol). The tubes were agitated. Fifty μL MTT (10 mg/mL methanol) were added to each tube, and the tubes were again agitated and incubated at 37° C. for 30 minutes.

Following incubation, the solutions were visually examined for MTT reduction, which was indicated by the presence of a purple color. The degree of reduction was graded by subjective evaluation of an experienced observer from 0 (no color produced and no reduction) to 4+(a deep purple color and very strong reduction). Numbers 1, 2 and 3 represent intermediate depths of color production and amounts of reduction.

The results are shown in Table I. In random, samples of leukocytes prepared from the blood of hospital patients, there was always some detectable reduction in the control solution, ranging from a small amount up to a considerable amount. The variability in this response is due to differences between patients in number of leukocytes present and the cells' level of activity. This unpredictable variability is part of the problem in attempting to counteract leukocyte interference in a bacterial assay. All the materials tested, however, reduced the leukocyte response to zero in every case, regardless of the magnitude of the interference.

Solution assays for bacterial MTT reduction were carried out with the addition of the same surfactants used in the leukocyte study above to determine whether the inhibitory effect was selective. To 2.5 mL of bacterial cell suspension in PBS ($\sim 10^9$ cells/mL) were added 2.5 mL PBS containing the indicated inhibitor. One hundred μL of each of the following were added to the suspension: 10% glucose, PMS (1 mg/mL methanol), and MTT (10 mg/mL methanol). The tubes were agitated and visually examined after incubation at 37° C. for 15 minutes.

The results, shown in Table I, indicate that the surfactants tested inhibited leukocyte reduction activity but not bacterial reduction activity. This is shown by the fact that the leukocyte response in the presence of surfactant was zero while the bacterial response was 4 or 4+in the presence of the surfactant. Thus, where a clinical sample contains unknown quantities of both types of cells, these lysing agents remove leukocyte interference from a reduction-based bacterial assay.

TABLE I

| | | Means for Selective Lysis of Leukocytes | | | | | | |
|---|---|---|---|---|---|---|---|---|
| | | | Leukocyte | | Bacterial Reduction | | | |
| Sample | Means for Lysing | Concentration | Reduction | Concentration | E. coli | P. vulgaris | S. aureus | S. faecalis |
| 1 | Triton X-100 | 0.05% (v/v) | 0 | 0.05% (v/v) | 4+ | 4 | 4 | 4 |
| 2 | Tergitol 15-S-12 | 0.1% (v/v) | 0 | 1.0% (v/v) | 4 | 4 | 4 | 4 |
| 3 | Brij 35 | 1.0 g % | 0 | 1.0 g % | 4 | 4 | 4 | 4 |
| 4 | Myrj 45 | 1.0 g % | 0 | 1.0 g % | 4 | 4 | 4 | 4 |
| 5 | saponin | 0.1 g % | 0 | 1.0 g % | 4 | 4 | 4 | 4 |
| 6 | digitonin | .025 g % | 0 | 0.25 g % | 4 | 4 | 4 | 4 |
| 7 | sonication | na* | 0 | — | — | — | — | — |
| control | none | na* | 1-3+ | na* | 4 | 4 | 4 | 4 |

*na = not applicable

EXAMPLE 8

Concentration Effects of TX-100 on Reduction by Both Bacteria and Leukocytes

Concentration effects of TX-100 on both bacterial and leukocyte reduction of MTT were examined. Bacterial cell suspensions and leukocyte cell suspensions were prepared. Solutions of the cells contained 0.3% v/v (Tween 80) and glucose, $4.0 \times 10^{-4}$ M MTT, $5.4 \times 10^{-5}$ M PMS, and various concentrations of (TX-b 100). Control solutions lacking cells were prepared for each concentration of TX-100.

The absorbance at 540 nm was measured for 10 minutes at 37° C. on a spectrophotometer. The results ($\Delta A$), presented in Table II, represent the absorbance at 540 nm at 10 minutes minus the absorbance at 540 nm at 0 minutes for the test minus the $\Delta A$ 540 nm for the appropriate control. MTT reduction by the bacteria tested was not inhibited in the presence of 0.1, 0.5, or 1.0% TX-100, whereas, reduction of MTT by leukocytes was inhibited by all concentrations of TX-100 tested. The large negative value obtained with leukocytes in the presence of 0.1% TX-100 was due to the measurement of the loss in solution turbidity upon gradual cell lysis. With higher concentrations of TX-100, cell lysis was rapid and essentially complete at 0 minutes so that loss of turbidity was immediate and not measured.

TABLE II

| | TX-100 Concentration Effects | | | |
|---|---|---|---|---|
| | $\Delta$ Absorbance 10 Minutes | | | |
| TX-100 Conc. (v/v) | E. coli $5 \times 10^7$/mL | S. aureus $7 \times 10^7$/mL | Ps aeruginosa $7 \times 10^7$/mL | Leukocytes* $1.5 \times 10^6$/mL |
| 0.1% | .32 | .27 | .06 | −.26 |
| 0.5% | .33 | .28 | .06 | −.02 |
| 1.0% | .32 | .27 | .07 | −.02 |
| control - no surfactant | .33 | .25 | .05 | .05 |

*mean of 4 random samples

EXAMPLE 9

Concentration Effects of Olin 10G on Reduction by Both Bacteria and Leukocytes

The effects of Olin 10G, a nonionic surfactant, on both bacterial and leukocyte reduction of MTT in solution were examined. Bacterial and leukocyte solutions were prepared which contained 0.2% glucose, $2.4 \times 10^{-4}$ M MTT, $2.0 \times 10^{-4}$ M PMS, and Olin 10G. Control solutions lacking cells were prepared for each concentration of Olin 10G tested. The $\Delta A$ at 540 nm in 10 minutes was determined as in Example 8 above.

The results, shown in Table III, demonstrate that MTT reduction by leukocytes is inhibited by 0.1, 0.5, and 1.0% (v/v) Olin 10G, whereas, the reduction of MTT by E. coli was not inhibited by Olin 10G at any of the concentrations tested.

TABLE III

| | $\Delta A$ 540 nm in 10 minutes | |
|---|---|---|
| Concentration of Olin 10 G (v/v) | E. coli $5 \times 10^7$/mL | Leukocytes* $2.3 \times 10^6$/mL |
| 0.1% | .53 | .01 |
| 0.5% | .62 | −.01 |
| 1.0% | .69 | .02 |
| Control-no surfactant | .32 | .22 |

*mean of 4 random samples

EXAMPLE 10

Effects of Leukocyte and Gram-Positive Bacterial Reduction Inhibitors in Combination Three random samples of leukocytes (average concentration $4.9 \times 10^6$ cells/mL PBS) were incubated for 10 minutes at 37° in solutions containing 0.2% glucose, 0.2 mM PMS, and 0.24 mM MTT. The solutions also contained 0.1% Tergitol 7, a surfactant which inhibits reduction activity in gram-positive bacteria, and/or 0.5% TX-100. A control solution contained all of the above components except surfactant. Absorbance at 540 nm was measured at 0 and 10 minutes. The $\Delta A$ at 10 minutes for each solution was calculated as described above.

The results, shown in Table IV, demonstrate that Tergitol 7 does not interfere with the ability of TX-100 to inhibit MTT reduction by leukocytes. Thus, the two surfactants are successfully used in combination to provide a gram-negative bacterial assay. The assay comprises adding to a clinical specimen as described above glucose, PMS, MTT, TX-100 to inhibit leukocytes, and Tergitol 7 to inhibit gram-positive bacteria. After incubation, the reduction shown by the purple color is a measure of gram-negative bacteria.

TABLE IV

| Effect of TX-100 and Tergitol 7 on Leukocyte Reduction | |
|---|---|
| Surfactant | ΔA 10 Minutes |
| 0.1% (v/v) Tergitol 7 | 0.137 |
| 0.5% (v/v) TX-100 | −0.084 |
| 0.1% Tergitol 7 + 0.5% TX-100 | −0.021 |
| Control (no surfactant) | 0.125 |

EXAMPLE 11

Effect of TX-100 on Bacterial and Leukocyte Reduction in Dry Element Format

Dry elements were prepared according to the description above. Test elements contained TX-100 in the reagent layer at 5.38 g/m$^2$ while control elements contained Zonyl FSN at 0.22 g/m$^2$. Four bacterial suspensions, individually comprising the gram-negative bacteria *Escherichia coli* and *Proteus vulgaris* and the gram-positive bacteria *Staphylococcus aureus* and *Streptococcus faecalis* were prepared in potassium phosphate buffer, pH 7.5, at concentrations of $1 \times 10^9$ cells/mL. Four randomly selected leukocyte samples were suspended in 0.05 M PBS pH 7.5 to concentrations of 7.3, 9.4, 11.6, and $13.8 \times 10^6$ cells/mL. Glucose was added to each sample to achieve a final concentration of 0.2%.

Ten μL of each sample were spotted on each element. Reflectance densities ($D_R$) were monitored at 540 nm over a 10-minute period. Buffer blanks were also measured and all $AD_R$ values, calculated as described above, were corrected for the background density of the appropriate buffer blank.

The results, shown in Table V, demonstrate that TX-100 inhibited chromogen reduction by the leukocytes but not by either gram-negative or gram-positive bacteria in the dry element system. A bacterial assay in dry mode, then, comprises using the test element described above, which contains a leukocyte inhibitor. The element is spotted with sample fluid which may contain bacteria and/or leukocytes and treated according to the above-described procedure. The $\Delta D_R$ then represents bacteria present in the sample.

TABLE V

| | Dry Element Assay | |
|---|---|---|
| | $\Delta D_R$ | |
| Samples | Control (no TX-100) | Test (5.38 g/m$^2$ TX-100) |
| 7.3 × 10$^6$ leukocyte/mL | 0.169 | 0.001 |
| 9.4 × 10$^6$ leukocyte/mL | 0.163 | −0.006 |
| 11.6 × 10$^6$ leukocyte/mL | 0.209 | 0.008 |
| 13.8 × 10$^6$ leukocyte/mL | 0.201 | 0.004 |
| 1 × 10$^9$ *E. coli*/mL | 0.357 | 0.367 |
| 1 × 10$^9$ *P. vulgaris*/mL | 0.349 | 0.361 |
| 1 × 10$^9$ *S. aureus*/mL | 0.320 | 0.301 |
| 1 × 10$^9$ *S. faecalis*/mL | 0.360 | 0.448 |

The invention has been described in detail with particular reference to preferred embodiments thereof, but it will be understood that variations and modifications can be effected within the spirit and scope of the invention.

What is claimed is:

1. A method for detecting viable leukocytes in an aqueous sample which comprises:
    A. contacting one portion of the sample with a reducible indicator which forms a detectable end product upon such contact;
    B. incubating the sample of step (A) for a time sufficient to cause formation of said detectable end product of step (A);
    C. detecting the amount of end product formed by reduction in step (B);
    D. contacting another portion of the aqueous sample with a means for lysing which selectively lyses leukocytes but neither gram-positive for gram-negative bacteria upon such contact, such that the reducing ability of neither gram-positive nor gram-negative bacteria is inhibited;
    E. contacting the sample of step (D) with a reducible substrate which forms a detectable end product upon such contact;
    F. incubating the sample of step (E) for a time sufficient to cause formation of said detectable end product of step (E);
    G. detecting the amount of end product formed by reduction in step (F);
    H. detecting the presence of viable leukocytes as a function of the difference between the result in step (C) and the resutl in step (G),
   wherein steps (A), (B), (E), and (F) are performed under conditions suitable for the formation of said detectable end products.

2. The method of claim 1 in which the reducible substrate is a chromogen which forms a colored end product upon reduction.

3. A method for detecting bacteria in an aqueous sample which comprises:
    A. contacting the sample with a surfactant that selectively lyses leukocytes but neither gram-positive nor gram-negative bacteria, in an amount sufficient to selectively lyse leukocytes but neither gram-positive nor gram-negative bacteria upon such contact, such that the reducing ability of neither gram-positive nor gram-negative bacteria is inhibited;
    B. contacting the sample of step (A) with reducible indicator which forms a detectable end product upon such contact;
    C. incubating the sample of step (B) for a time sufficient to cause formation of said detectable end product;
    D. detecting the amount of bacteria present as a function of the amount of end product formed by reduction in step (C),
   wherein steps (B) and (C) are performed under condition suitable for the formation of said detectable end product.

4. A method for detecting bacteria in an aqueous sample which comprises:
    A. sonicating the sample so as to cause lysis of leukocyte cells but neither gram-positive not gram-negative bacteria, such that the reducing ability of neither gram-positive nor gram-negative bacteria is inhibited;
    B. contacting the sample with a reducible indicator which forms a detectable end product upon such contact;
    C. incubating the sample of step (B) for a time sufficient to cuase formation of said detectable end porduct;
    D. detecting the amount of bacteria present as a function of the amount of end product formed by reduction in step (C),
   wherein steps (B) and (C) are performed under conditions suitable for the formation of said end product, 5. The method of claim 3 in which the reducible indicator is a chromogen which forms a colored end product.

6. The method of claim 4 in which the reducible indicator is a chromogen which forms a colored end product.

7. The method of claim 3 in which the surfactant is a nonionic surfactant which selectively lyses leukocytes but neither gram-positive nor gram-negative bacteria.

8. The method of claim 3 in which the surfactant is an anionic surfactant which selectively lyses leukocytes but neither gram-positive nor gram-negative bacteria.

9. The method of claim 3 in which the surfactant is selected from the group consisting of: octylphenoxy polyethoxyethanol, n-nonyl phenoxy polyglycerol, polyethylene glycol ether of a secondary alcohol, polyoxyethylene lauryl ether, and polyoxyethylene stearate.

10. The method of claim 3 in which the surfactant is selected from the group consisting of: saponin and digitonin.

11. A method for detecting the presence of gram-negative bacteria in an aqueous sample which comprises:
  A. contacting the sample with a surfactant that selectively lyses leukocytes but neither gram-positive nor gram-negative bacteria, in an amount sufficient to selectively lyse leukocytes but neither gram-positive nor gram-negative bacteria, such that the reducing ability of neither gram-positive nor gram-negative bacteria is inhibited, a second surfactant which selectively inhibits the reducing ability of gram-positive bacteria but not gram-negative bacteria, in an amount sufficient to inhibit the reducing ability of gram-positive bacteria but not gram-negative bacteria, and a reducible indicator which forms a detectable end product upon such contact;
  B. incubating the sample of step (A) for a time sufficient to cause formation of said detectable end product;
  C. detecting the amount of gram-negative bacteria present as a function of the amount of end product formed by reduction in step (B),
wherein steps (A) and (B) are performed under conditions suitable for the formation of said detectable end product.

12. The method of claim 11 in which the reducible indicator is a chromogen which forms a colored end product upon reduction.

13. A method for detecting the presence of gram-positive bacteria in an aqueous sample which comprises:
  A. contacting the sample with a surfactant that selectively lyses leukocytes but niether gram-positive nor gram-negative bacteria, in an amount sufficient to selectively lyse leukocytes but neither gram-positive nor gram-negative bacteria, such that the reducing ability of neither gram-positive nor gram-negative bacteria is inhibited, a salt which selectively inhibits the reducing ability of gram-negative bacteria but not gram-positive bacteria, in an amount sufficient to inhibit the reducing ability of gram-negative but not gram-positive bacteria, and a reducible indicator which forms a detectable end product upon such contact;
  B. incubating the sample of step (A) for a time sufficient to cause formation of said detectable end product;
  C. detecting the amount of gram-positive present as a function of the amount of end product formed by reduction in step (B),
wherein steps (A) and (B) are performed under conditions suitable for the formation of said detectable end product.

14. The method of claim 13 in which the reducible indicator is a chromogen which forms a colored end product upon reduction.

15. A dry test element which comprises a support having thereon a layer which incorporates a surfactant that selectively lyses leukocytes but neither gram-positive nor gram-negative bacteria, in an amount sufficient to cause leukocyte cell lysis, such that the reducing ability of neither gram-positive nor gram-negative bacteria is inhibited, a reducible chromogen, and an electron transfer agent.

16. The element of claim 15 wherein said surfactant selectively causes leukocyte cell lysis, but neither gram-positive nor gram-negative bacteria cell lysis.

17. The element of claim 15 in which the surfactant-containing layer incorporates a second surfactant which selectively inhibits the reducing ability of gram-positive bacteria but not gram-negative bacteria, in an amount sufficient to inhibit the reducing ability of gram-positive bacteria.

18. The element of claim 15 in which the surfactant-containing layer incorporates a salt which selectively inhibits the reducing ability of gram-negative bacteria but not gram-positive bacteria, in an amount sufficient to inhibit the reducing ability of gram-negative bacteria.

19. A method for detecting the presence of bacteria in an aqueous sample which comprises:
  A. spotting with sample fluid a dry test element which comprises a support having thereon a layer which incorporates a surfactant that selectively lyses leukocytes but neither gram-positive nor gram-negative bacteria, in an amount sufficient to cause leukocyte cell lysis, such that the reducing ability of neither gram-positive nor gram-negative bacteria is inhibited, a reducible chromogen, and an electron transfer agent;
  B. incubating the element of step (A) for a time sufficient to cause reduction of said reducible chromogen;
  C. detecting the amount of bacteria present as a function of the amount of color formed by reduction in step (B),
wherein steps (A) and (B) are performed under conditions suitable for the reduction of said reducible chromogen.

20. A method for detecting the presence of viable leukocytes in an aqueous sample which comprises:
  A. spotting a dry test element, comprising a support layer having thereon a reagent layer which incorporates a reducible chromogen and an electron transfer agent, with sample fluid;
  B. incubating the element of step (A) for a time sufficient to cause reduction of said reducible hromogen of step (A);
  C. detecting the amount of color formed by reduction in step (B);
  D. spotting with the sample fluid a dry test element which comprises a support having thereon a layer which incorporates a surfactant that selectively lyses leukocytes but neither gram-positive nor gram-negative bacteria, in an amount sufficient to cause leukocyte cell lysis, such that the reducing ability of neither gram-positive nor gram-negative bacteria is inhibited, a reducible chromogen, and an electron transfer agent;

E. incubating the element of step (D) for a time sufficient to cause reduction of said reducible chromogen of step (D);

F. detecting the amount of color formed by reduction in step (E);

G. detecting the presence of viable leukocytes as a function of the difference between the result in step (C) and the result in step (F), wherein steps (A), (B), (D), and (E) are performed under conditions suitable for the reduction of said reducible chromogens.

21. A method for detecting the presence of gram-negative bacteria in an aqueous sample which comprises:

A. spotting with sample fluid a dry test element which comprises a support having thereon a layer which incorporates a first surfactant that lyses leukocytes but neither gram-positive nor gram-negative bacteria, in an amount sufficient to cause leukocyte cell lysis, such that the reducing ability of neither gram-positive nor gram-negative bacteria is inhibited, a reducible chormogen, an electron transfer agent, and a second surfactant that selectively inhibits the reducing ability of gram-positive bacteria but not gram-negative bacteria, in an amount sufficient to inhibit the reducing ability of gram-positive bacteria;

B. incubating the element of step (A) for a time sufficient to cause reduction of said reducible chromogen;

C. detecting the amount of gram-negative bacteria present as a function of the amount of color formed by reduction in step (B), wherein steps (A) and (B) are performed under conditions suitable for the reduction of said reducible chromogen.

22. A method for detecting the presence of gram-positive bacteria in an aqueous sample which comprises:

A. spotting with sample fluid a dry test element which comprises a support having thereon a layer which incorporates a surfactant that lyses leukocytes but neither gram-positive nor gram-negative bacteria, in an amount sufficient to cause leukocyte cell lysis, such that the reducing ability of neither gram-positive nor gram-negative bacteria is inhibited, a reducible chromogen, an electron transfer agent, and a salt that selectively inhibits the reducing aiblity of gram-negative bacteria but not gram-positive bacteria, in an amount sufficient to inhibit the reducing ability of gram-negative bacteria;

B. incubating the element of step (A) for a time sufficient to cause reduction of said reducible chromogen;

C. detecting the amount of gram-positive bacteria present as a function of the amount of color formed by reduction in step (B), wherein steps (A) and (B) are performed under conditions suitable for the reduction of said reducible chromogen.

23. A composition comprising a reducible indicator which forms a detectable end product, a surfactant that selectively lyses leuokocytes but neither gram-positive nor gram-negative bacteria, in an amount sufficient to cause leukocyte cell lysis, such that the reducing ability of neither gram-positive nor gram-negative bacteria is inhibited, and an aqueous sample suspected of containing leukocyte cells.

24. The composition of claim 23 in which the reducible indicator is a chromogen which forms a colored end product upon reduction.

* * * * *